United States Patent [19]

Rentzea et al.

[11] Patent Number: 4,678,798

[45] Date of Patent: Jul. 7, 1987

[54] N-(AZOLYLCARBAMYL)-HYDROXYLA-MINES AND FUNGICIDES CONTAINING THESE COMPOUNDS

[75] Inventors: Costin Rentzea, Heidelberg; Hubert Sauter, Mannheim; Stefan Karbach, Ludwigshafen; Wolfgang Will, Mannheim; Eberhard Ammermann, Ludwigshafen; Ernst-Heinrich Pommer, Limburgerhof, all of Fed. Rep. of Germany

[73] Assignee: BASF Aktiengesellschaft, Fed. Rep. of Germany

[21] Appl. No.: 724,761

[22] Filed: Apr. 18, 1985

[30] Foreign Application Priority Data

Apr. 21, 1984 [DE] Fed. Rep. of Germany ....... 3415138

[51] Int. Cl.$^4$ .................. C07D 249/08; C07D 233/56; A61K 31/41
[52] U.S. Cl. .................................... 514/383; 514/399; 548/262; 548/341
[58] Field of Search ................ 548/262, 341; 514/399, 514/383; 71/92

[56] References Cited

U.S. PATENT DOCUMENTS 4,080,462 3/1978 Brookes et al. ..................... 514/399
4,139,365 2/1979 Copping et al. ........................ 71/92
4,500,536 2/1985 Yoshida et al. ...................... 514/397

OTHER PUBLICATIONS

Staab et al, Chem. Abstracts, vol. 56, Col. 7303 (f), (1961), QD1A51.
Chemical Week, Jun. 21, 1972, p. 46.

Primary Examiner—Glennon H. Hollrah
Assistant Examiner—D. L. Dinner
Attorney, Agent, or Firm—Keil & Weinkauf

[57] ABSTRACT

N-(Azolylcarbamyl)-hydroxylamines of the formula

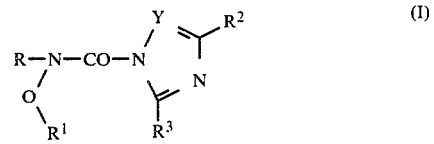

where R is unsubstituted or substituted alkyl, alkenyl, alkoxyalkyl or cycloalkyl, or unsubstituted or substituted phenyl, phenylalkyl, phenylalkenyl or phenoxyalkyl, $R^1$ is alkyl, alkenyl, alkoxyalkyl, alkylthioalkyl, cycloalkyl, cycloalkylalkyl or unsubstituted or substituted benzyl, Y is CH or N and $R^2$ and $R^3$ are each hydrogen or alkyl, and fungicides which contain these compounds.

3 Claims, No Drawings

N-(AZOLYLCARBAMYL)-HYDROXYLAMINES AND FUNGICIDES CONTAINING THESE COMPOUNDS

The present invention relates to novel N-(azolylcarbamyl)-hydroxylamines, processes for their preparation and fungicides which contain these compounds as active ingredients.

It has been disclosed that N-trichloromethylthiotetrahydrophthalimide can be used as a fungicide in agriculture as well as in fruit cultivation and horticulture (cf. Chemical Week, June 21, 1972, page 46). However, the conventional agent can be used only before infection, and its action does not meet practical requirements at low application rates.

We have found that N-(azolylcarbamyl)-hydroxylamines of the formula

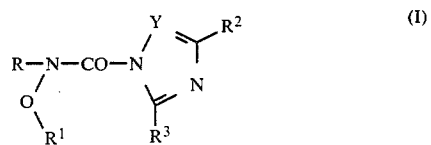  (I)

where R is unsubstituted or substituted alkyl, alkenyl, alkoxyalkyl or cycloalkyl, each of not more than 12 carbon atoms, or phenyl, phenyl-$C_1$-$C_4$-alkyl, phenylalkenyl or phenoxy-$C_1$-$C_6$-alkyl, each of which is unsubstituted or substituted by halogen, cyano, nitro, trifluoromethyl, $C_1$-$C_4$-alkyl or $C_1$-$C_4$-alkoxy, $R^1$ is alkyl, alkenyl, alkoxyalkyl, alkylthioalkyl, cycloalkyl or cycloalkylalkyl, each of which is of not more than 12 carbon atoms, or benzyl which is unsubstituted or substituted by halogen, $C_1$-$C_4$-alkyl, $C_1$-$C_4$-alkoxy, trifluoromethyl, nitro or cyano, Y is CH or N, and $R^2$ and $R^3$ are identical or different and are each hydrogen or alkyl of 1 to 5 carbon atoms, are very effective against harmful fungi.

The novel compounds of the formula I contain chiral centers and are generally obtained in the form of mixtures (racemates or diastereomer mixtures). For some of the novel compounds, the diastereomers can be separated, for example by column chromatography, or isolated in pure form on the basis of solubility differences. Pure enantiomers can be obtained from such diastereomers by a conventional method. The present invention embraces these as well as their mixtures. When the novel compounds are employed as fungicides, both the diastereomers or enantiomers and mixtures of these obtained in the synthesis are suitable, the mixtures preferably being used.

In formula I, suitable radicals R and $R^1$ are $C_1$-$C_{12}$-alkyl, such as ethyl, n-propyl, isopropyl, n-butyl, isobutyl, sec.-butyl, tert.-butyl, n-pentyl, 3-methylbut-1-yl, n-hexyl, 3,3-dimethylbut-1-yl, n-heptyl, n-octyl, 2,4,4-trimethylpentyl, 2-ethylhexyl, n-decyl or n-dodecyl, cyclopropylmethyl, $C_5$- or $C_6$-cycloalkyl, such as cyclopentyl or cyclohexyl, 4-methylcyclohexyl, cyclohexylmethyl, 4-tert.-butylcyclohexyl, $C_1$-$C_4$-alkoxy-$C_1$-$C_4$-alkyl, such as 2-methoxyethyl, 2-ethoxyethyl, 2-propoxyethyl, 2-butoxyethyl, 3-methoxypropyl, 3-ethoxypropyl, 3-propoxypropyl or 3-butoxypropyl, $C_3$-$C_8$-alkenyl, such as allyl, but-2-en-1-yl, pent-2-en-1-yl or oct-2-en-1-yl, benzyl, 4-methylbenzyl, alpha-methylbenzyl, alpha-ethylbenzyl, 2-, 3- and 4-fluorobenzyl, 2-, 3- and 4-chlorobenzyl, 4-bromobenzyl, 3- and 4-trifluoromethylbenzyl, 4-tert.-butylbenzyl, p-methoxybenzyl, 2,4-dichlorobenzyl and phenylethyl. R may furthermore be phenyl, 2-, 3- and 4-chlorophenyl, 4-methylphenyl, 4-methoxyphenyl, 4-trifluoromethyl, 2,4-dichloro- or 3,4-dichlorophenyl, phenoxyethyl, phenoxypropyl, phenoxybutyl, phenoxyhexyl, 4-fluorophenoxyethyl, 4-fluorophenoxybutyl, 2-, 3- or 4-chlorophenoxyethyl, -propyl, -butyl or -hexyl, 2,4-, 3,4- or 2,6-dichlorophenoxyethyl, -propyl, -butyl or -hexyl, 2,4,6-, 3,5,6- or 2,5,6-trichlorophenoxyethyl, -propyl or -butyl, 4-methoxyphenoxyethyl, -propyl or -butyl, 2-methyl-4,6-dichlorophenoxyethyl, -propyl or -butyl, 2,6-dichloro-4-bromophenoxyethyl, -propyl or -butyl or 4-phenylphenoxyethyl, -propyl or -butyl.

$R^2$ and $R^3$ are each preferably hydrogen, methyl, ethyl, n-propyl or isopropyl.

The compounds of the formula I can be prepared by a method in which a carbamyl chloride of the formula II

  (II)

where R and $R^1$ have the above meanings, is reacted with
(a) an azole of the formula III

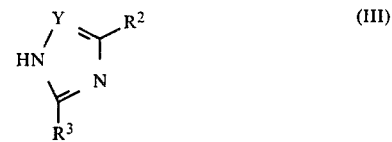  (III)

where $R^2$, $R^3$ and Y have the above meanings, or
(b) a metal derivative thereof, of the formula IV

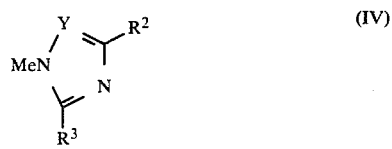  (IV)

where $R^2$, $R^3$ and Y have the above meanings and Me is lithium, sodium, potassium or one equivalent of calcium, or
(c) a silyl derivative thereof, of the formula V

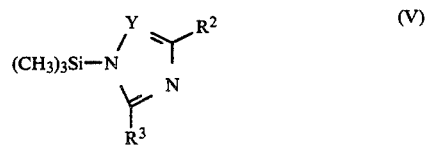  (V)

where $R^2$, $R^3$ and Y have the above meanings.

Reaction (a) is carried out in the presence of absence of a solvent or diluent, and with or without the addition of an inorganic or organic base and of a reaction accelerator, at from 10° to 120° C.

Examples of preferred solvents or diluents which are inert to the reactants are aliphatic and aromatic hydrocarbons and halohydrocarbons, such as n-pentane, cyclohexane, methylene chloride, 1,1,1-trichloroethane, benzene, toluene, xylene or chlorobenzene, aliphatic ketones, such as acetone, methyl ethyl ketone or diethyl ketone, ethers, such as diethyl ether, methyl tert.-butyl ether, dimethoxyethane, tetrahydrofuran or dioxane, esters, such as ethyl acetate, nitriles, such as acetonitrile, and amides, such as dimethylformamide, dimethylacetamide and N-methylpyrrolidone, and mixtures of these.

Examples of suitable bases which may furthermore be used as acid acceptors in the reaction are alkali metal hydroxides, such as lithium hydroxide, sodium hydroxide, potassium hydroxide or calcium hydroxide, alkali metal carbonates, such as sodium carbonate, potassium carbonate, sodium bicarbonate or potassium bicarbonate, and amines, such as triethylamine, tripropylamine, N-methylpyrrolidine, N-methylpiperidine, N,N-dimethylcyclohexylamine, N,N'-tetramethylethylenediamine, N,N-dimethylaniline, N,N-diethylaniline, pyridine and 4-dimethylaminopyridine. However, other conventional bases may also be used.

Preferred reaction accelerators are metal halides, such as sodium iodide or potassium iodide, quaternary ammonium salts, such as tetrabutylammonium chloride, bromide or iodide or benzyltriethylammonium chloride or bromide, and crown ethers, such as 12-crown-4, 15-crown-5, 18-crown-6 or dibenzo-18-crown-6.

Reactions (b) and (c) are carried out in the presence or absence of a solvent or diluent, at from 0° to 140° C., preferably from 0° to 100° C. Solvents which can be used in this case are those which are suitable for version (a) of the process.

The compounds of the formula I can furthermore be prepared by reacting a compound of the formula VI

where R and R¹ have the above meanings, with a carbonylbisazole of the formula VII

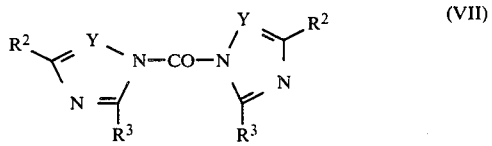

where R², R³ and Y have the above meanings, in the presence or absence of a solvent or diluent, and with or without the addition of a reaction accelerator.

Examples of solvents or diluents which are suitable in this case are diethyl ether, 1,2-dimethoxyethane, dipropyl ether, dibutyl ether, methyl tert.-butyl ether, tetrahydrofuran, dimethoxyethane, anisole, n-pentane, n-hexane, n-heptane, n-octane, isooctane, cyclohexane, toluene, chlorobenzene, xylenes, acetonitrile, ethyl acetate, dimethylformamide, N-methylpyrrolidone, acetone and methyl ketone.

Examples of suitable reaction accelerators are 4-dimethylaminopyridine and 4-pyrrolidinopyridine.

The starting materials of the formula II can readily be prepared by a conventional process, for example by reacting an amine of the formula VI with phosgene (Houben-Weyl-Muller, Methoden der organischen Chemie, Volume 8, pages 115–118, Georg Thieme Verlag Stuttgart 1952).

The Examples which follow illustrate the preparation of the compounds of the formula I.

EXAMPLE 1

(a) 30.4 g (0.1 mole) of 2,4,6-trichlorophenoxyethyl bromide were added to a suspension of 48.5 g (0.5 mole) of O-ethylhydroxylamine hydrochloride in 250 ml of ethyldiisopropylamine, and the mixture was stirred for 4 days at 50° C. and then cooled to 15° C. and filtered under suction. The filtrate was evaporated down under reduced pressure, in the final stage at 60° C. and under 0.1 mbar, the residue was dissolved in 300 ml of ether, and the solution was gassed with hydrogen chloride at +3° C. 17 g of O-ethyl-N-(2,4,6-trichlorophenoxy)ethylhydroxylamine hydrochloride of melting point 173°–175° C. were obtained.

(b) A thoroughly stirred suspension of 15.9 g (0.05 mole) of O-ethyl-N-(2,4,6-trichlorophenoxy)-ethylhydroxylamine in 150 ml of dry ethyl acetate was gassed with phosgene for 8 hours at 50° C., and the mixture was evaporated down under reduced pressure. 17.3 g of O-ethyl-N-chlorocarbonyl-N-(2,4,6-trichlorophenoxy)-ethylhydroxylamine were obtained as a colorless oil, which was directly reacted further.

(c) 17.3 g (0.05 mole) of the above product were added dropwise to a solution of 10.3 g (0.15 mole) of imidazole in 100 ml of dry tetrahydrofuran at 25° C., the mixture was stirred for 8 hours at 70° C. and then cooled to 20° C., and the resulting precipitate was filtered off under suction. The filtrate was evaporated down under reduced pressure, the residue was taken up in 200 ml of methylene chloride, and the solution was washed with three times 70 ml of water, dried and evaporated down.

12.5 g of O-ethyl-N-carbonylimidazole-N-(2,4,6-trichlorophenoxy)-ethylhydroxylamine were obtained as white crystals of melting point 66°–67° C. (Compound No. 1).

The compounds listed in the Table below can be prepared in a similar manner:

| Compound no. | R | R¹ | Y | R² | R³ | M.p. [°C.] IR (film) [cm⁻¹] |
|---|---|---|---|---|---|---|
| 2 | $C_2H_5$ | $CH_3$ | CH | H | H | |
| 3 | $C_2H_5$ | $C_2H_5$ | CH | H | H | |
| 4 | $C_2H_5$ | n-$C_3H_7$ | CH | H | H | |
| 5 | i-$C_3H_7$ | $C_2H_5$ | CH | H | H | |
| 6 | i-$C_3H_7$ | n-$C_4H_9$ | CH | H | H | |
| 7 | i-$C_3H_7$ | n-$C_4H_9$ | N | H | H | |
| 8 | i-$C_3H_7$ | n-$C_6H_9$ | CH | H | H | |
| 9 | i-$C_3H_7$ | n-$C_6H_9$ | N | H | H | |
| 10 | i-$C_3H_7$ | cyclopropylmethyl | CH | H | H | |
| 11 | i-$C_3H_7$ | cyclopentyl | CH | H | H | |
| 12 | i-$C_3H_7$ | cyclohexyl | CH | H | H | |
| 13 | i-$C_3H_7$ | —$CH_2$—CH=$CH_2$ | CH | H | H | 1692, 1460, 1409, 1369, 1314, |

-continued

| Compound no. | R | R¹ | Y | R² | R³ | M.p. [°C.] IR (film) [cm⁻¹] |
|---|---|---|---|---|---|---|
| | | | | | | 1285, 1203, 1178, 1100, 1063, 1006, 960, 942 |
| 14 | i-C$_3$H$_7$ | —CH$_2$—CH=CH$_2$ | N | H | H | 53–55 |
| 15 | i-C$_3$H$_7$ | —CH$_2$—CH—CH$_3$H$_7$ | CH | H | H | |
| 16 | i-C$_3$H$_7$ | —(CH$_2$)$_2$OC$_2$H$_5$ | CH | H | H | |
| 17 | n-C$_6$H$_{13}$ | —(CH$_2$)$_2$OC$_3$H$_7$ | CH | H | H | |
| 18 | n-C$_{12}$H$_{25}$ | —(CH$_2$)$_3$OC$_4$H$_5$ | CH | H | H | |
| 19 | n-C$_{12}$H$_{25}$ | —(CH$_2$)$_3$OC$_4$H$_5$ | N | H | H | |
| 20 | —CH$_2$—CH=CH$_2$ | n-C$_{12}$H$_{25}$ | CH | H | H | |
| 21 | —CH$_2$—CH=CH$_2$ | n-C$_{12}$H$_{25}$ | N | H | H | |
| 22 | —CH$_2$—CH=CH—C$_3$H$_7$ | 4-ClC$_6$H$_4$—CH$_2$— | CH | H | H | |
| 23 | cyclohexyl | —CH$_2$—CH=CH$_2$ | CH | H | H | 28–31 |
| 24 | cyclohexyl | —CH$_2$—CH=CH$_2$ | N | H | H | 82–84 |
| 25 | cyclohexyl | —CH$_2$—C$_6$H$_5$ | CH | H | H | 74–76 |
| 26 | cyclohexyl | —CH$_2$—C$_6$H$_5$ | N | H | H | 95–97 |
| 27 | cyclohexyl | 4-F—C$_6$H$_4$—CH$_2$— | CH | H | H | |
| 28 | cyclohexyl | 4-BrC$_6$H$_4$—CH$_2$— | CH | H | H | |
| 29 | cyclohexyl | 2,4-Cl$_2$C$_6$H$_3$—CH$_2$— | CH | H | H | |
| 30 | cyclohexyl | 3,4-Cl$_2$C$_6$H$_3$—CH$_2$— | CH | H | H | |
| 31 | 4-methylcyclohexyl | 4-CF$_3$—C$_6$H$_4$—CH$_2$— | CH | H | H | |
| 32 | 4-methylcyclohexyl | 3-CF$_3$—C$_6$H$_4$—CH$_2$— | CH | H | H | |
| 33 | cycloheptyl | —CH$_2$—C$_6$H$_5$ | CH | H | H | |
| 34 | cyclooctyl | —CH$_2$—C$_6$H$_5$ | CH | H | H | |
| 35 | cyclododecyl | —CH$_2$—C$_6$H$_5$ | CH | H | H | |
| 36 | 4-tert.-butylcyclohexyl | —CH$_2$—C$_6$H$_5$ | CH | H | H | |
| 37 | C$_6$H$_5$—CH$_2$— | —(CH$_2$)$_2$CH(CH$_3$)$_2$ | CH | H | H | |
| 38 | C$_6$H$_5$—CH$_2$— | —(CH$_2$)$_2$CH(CH$_3$)$_2$ | N | H | H | |
| 39 | 4-ClC$_6$H$_4$—CH$_2$— | —CH$_2$CH(C$_2$H$_5$)(CH$_2$)$_3$CH$_3$ | CH | H | H | |
| 40 | 3,4-Cl$_2$—C$_6$H$_3$—CH$_2$ | —(CH$_2$)$_2$CH(CH$_3$)CH$_2$C(CH$_3$)$_3$ | CH | H | H | |
| 41 | 1-phenyl-1-ethyl | iso-C$_3$H$_7$ | CH | H | H | 54–56 |
| 42 | 1-phenyl-1-ethyl | iso-C$_3$H$_7$ | N | H | H | 86–88 |
| 43 | C$_6$H$_5$—O—(CH$_2$)$_2$— | n-C$_6$H$_{13}$ | CH | H | H | |
| 44 | C$_6$H$_5$—O—(CH$_2$)$_2$— | n-C$_6$H$_{13}$ | N | H | H | |
| 45 | C$_6$H$_5$—O—(CH$_2$)$_3$— | n-C$_4$H$_9$ | CH | H | CH$_3$ | |
| 46 | C$_6$H$_5$—O—(CH$_2$)$_4$— | n-C$_4$H$_9$ | CH | H | isoC$_3$H$_7$ | |
| 47 | C$_6$H$_5$—O—(CH$_2$)$_4$— | C$_2$H$_5$ | CH | H | H | 1688, 1600, 1498, 1437, 1420, 1294, 1245, 1019, 756, 693 |
| 48 | C$_6$H$_5$—O—(CH$_2$)$_5$— | C$_2$H$_5$ | CH | H | H | 1722, 1599, 1585, 1545, 1497, 1474, 1315, 1288, 1244, 1080, 755, 692 |
| 49 | 2-ClC$_6$H$_4$—O(CH$_2$)$_4$— | n-C$_4$H$_9$ | CH | H | H | |
| 50 | 3-ClC$_6$H$_4$—O(CH$_2$)$_4$— | —CH$_2$—C$_6$H$_5$ | CH | H | H | |
| 51 | 4-ClC$_6$H$_4$—O—(CH$_2$)$_2$— | n-C$_6$H$_{13}$ | CH | H | H | |
| 52 | 2-FC$_6$H$_4$—O—(CH$_2$)$_4$— | C$_2$H$_5$— | CH | H | H | 1688, 1507, 1472, 1457, 1436, 1419, 1311, 1281, 1259, 1205, 1109, 1063, 1019, 749 |
| 53 | 3,4-Cl$_2$C$_6$H$_3$—O—(CH$_2$)$_5$— | C$_2$H$_5$— | CH | H | H | 69–71 |
| 54 | 3,4-Cl$_2$C$_6$H$_3$—O—(CH$_2$)$_2$— | C$_2$H$_5$— | N | H | H | 108–111 |
| 55 | 2,6-Cl$_2$C$_6$H$_3$—O—(CH$_2$)$_2$— | C$_2$H$_5$— | N | H | H | |
| 56 | 4-CH$_3$—C$_6$H$_4$—O—(CH$_2$)$_4$— | —CH$_2$—CH=CH$_2$ | CH | H | H | |
| 57 | 4-tert.-C$_4$H$_9$—C$_6$H$_4$—O—(CH$_2$)$_4$— | n-C$_6$H$_{13}$ | CH | H | H | |
| 58 | 4-CH$_3$O—C$_6$H$_4$—O—(CH$_2$)$_4$— | n-C$_4$H$_9$ | CH | H | H | |
| 59 | 4-C$_2$H$_5$O—C$_6$H$_4$—O—(CH$_2$)$_4$— | n-C$_4$H$_9$ | CH | H | H | |
| 60 | 4-CF$_3$C$_6$H$_4$—O—(CH$_2$)$_2$— | n-C$_6$H$_{13}$ | CH | H | H | |
| 61 | 4-CNC$_6$H$_4$—O—(CH$_2$)$_6$— | n-C$_5$H$_{11}$ | CH | H | H | |
| 62 | 2,4,6-Cl$_3$C$_6$H$_2$—O—(CH$_2$)$_3$— | C$_2$H$_5$ | CH | H | H | 1689, 1551, 1446, 1418, 1385, 1298, 1258, 1246, 1229, 1062, 1022, 1006, 856 |
| 63 | 2,4,6-Cl$_3$C$_6$H$_2$—O—(CH$_2$)$_3$— | —CH$_2$—CH=CH$_2$ | CH | H | H | 1690, 1552, 1447, 1419, 1384, 1297, 1258, 1248, 1228, 1062, 1007, 937, 857, 799 |
| 64 | 2,4,6-Cl$_3$C$_6$H$_2$—O—(CH$_2$)$_4$— | C$_2$H$_5$ | CH | H | H | 1688, 1551, 1439, 1419, 1386, 1279, 1257, 1216, 1064, 1019, 856, 814, 799, 733 |
| 65 | 2,6-Cl$_2$—4Br—C$_6$H$_2$—O(CH$_2$)$_2$— | C$_2$H$_5$ | CH | H | H | 1690, 1463, 1448, 1434, 1380, 1253, 1240, 1062, 1021, 1005, 807, 750, 733 |
| 66 | 2-CH$_3$,4,6-Cl$_2$C$_6$H$_2$—O(CH$_2$)$_2$— | C$_2$H$_5$ | CH | H | H | 1692, 1463, 1434, 1389, 1281, 1261, 1212, 1177, 1062, 1043, 1021, 1006, 854, 759 |
| 67 | 4-C$_6$H$_5$—2ClC$_6$H$_3$—O(CH$_2$)$_2$— | C$_2$H$_5$ | CH | H | H | 70–72 |

The novel active ingredients have a strong fungitoxic action on phytopathogenic fungi. They are particularly useful for preventing and curing plant diseases caused by microorganisms, e.g., *Phytophthora infestans, Botrytis cinerea, Plasmopara viticola, Monilia fructigena, Alternaria solani, Sclerotinia sclerotiorum, Pyricularia oryzae, Pellicularia filamentosa,* and *Sclerotinia cinera.*

The novel active ingredients are also effective on *Candida albicans* and *Trichophyton mentagrophytes.*

The active ingredients may simultaneously suppress the growth of two or more of the said fungi, and are excellently tolerated by plants. Some of the active ingredients also have curative properties, i.e., the agents may be applied after infection of the plants by the pathogen and success is still ensured.

The fungicidal agents contain from 0.1 to 95, and preferably from 0.5 to 90, wt % of active ingredient. The application rates depend on the type of effect desired, and range from 0.1 to 5 kg of active ingredient per hectare.

The novel active ingredients may also be mixed and applied with other active ingredients, e.g., herbicides, insecticides, growth regulators, other fungicides and fertilizers. When mixed with other fungicides, the spectrum of fungicidal action is in many cases increased; with a number of these fungicidal compositions, synergistic effects also occur, i.e., the fungicidal action of the combination product is greater than the effect of the individual components added together. Examples of fungicides which can be combined with the novel compounds are as follows:

sulfur
dithiocarbamates and derivatives thereof, such as
ferric dimethyldithiocarbamate
zinc dimethyldithiocarbamate
zinc ethylenebisthiocarbamate
tetramethylthiuram disulfide
manganese-zinc ethylenediamine-bisdithiocarbamate
ammonia complex of zinc-(N,N'-ethylene)-bisdithiocarbamate and
N,N'-polyethylene-bis-(thiocarbamoyl)-disulfide
ammonia complex of zinc-(N,N'-propylene-bis-dithiocarbamate) and
N,N'-polypropylene-bis-(thiocarbamoyl)-disulfide nitro derivatives, such as
dinitro-(1-methylheptyl)-phenylcrotonate
2-sec-butyl-4,6-dinitrophenyl-3,5-dimethylacrylate
2-sec-butyl-4,6-dinitrophenylisopropylcarbonate
diisopropyl 5-nitroisophthalate
heterocyclic structures, such as
2-heptadecyl-2-imidazoline acetate
2,4-dichloro-6-(o-chloroanilino)-s-triazine
O,O-diethylphthalimidophosphorothionate
5-amino-1-[bis-(dimethylamino)-phosphynyl]-3-phenyl-1,2,4-triazole
2,3-dicyano-1,4-dithiaanthraquinone
2-thio-1,3-dithio-(4,5-b)-quinoxaline
methyl 1-(butylcarbamoyl)-2-benzimidazole carbamate
2-methoxycarbonylaminobenzimidazole
2-[furyl-(2)]-benzimidazole
2-[thiazolyl-(4)]-benzimidazole
N-(1,1,2,2-tetrachloroethylthio)-tetrahydrophthalimide
N-trichloromethylthiotetrahydrophthalimide
N-trichloromethylphthalimide
N-dichlorofluoromethylthio-N',N'dimethyl-N-phenyl-sulfuric acid diamide
5-ethoxy-3-trichloromethyl-1,2,3-thiadiazole
2-thiocyanomethylthiobenzthiazole
1,4-dichloro-2,5-dimethoxybenzole
4-(2-chlorophenylhydrazono)-3-methyl-5-isoxazolone
pyridine-2-thio-1-oxide
8-hydroxyquinoline and its copper salt
2,3-dihydro-5-carboxanilido-6-methyl-1,4-oxathiin-4,4-dioxide
2,3-dihydro-5-carboxanilido-6-methyl-1,4-oxathiin
2-methyl-5,6-dihydro-4-H-pyran-3-carboxanilide
2-methyl-furan-3-carboxanilide
2,5-dimethyl-furan-3-carboxanilide
2,4,5-trimethyl-furan-3-carboxanilide
2,5-dimethyl-furan-3-carboxylic acid cyclohexylamide
N-cyclohexyl-N-methoxy-2,5-dimethyl-furan-3-carboxamide
2-methyl-benzoic acid anilide
2-iodobenzoic anilide
N-formyl-N-morpholine-2,2,2-trichloroethylacetal
piperazine-1,4-diylbis-(1-(2,2,2-trichloroethyl)-formamide
1-(3,4-dichloroanilino)-1-formylamino-2,2,2-trichlorethane
2,6-dimethyl-N-tridecyl-morpholine and its salts
2,6-dimethyl-N-cyclododecyl-morpholine and its salts
N-[3-(p-tert.-butylphenyl)-2-methylpropyl]-cis-2,6-dimethylmorpholine
N-[3-(p-tert.-butylphenyl)-2-methylpropyl]-piperidine
1-[2-(2,4-dichlorophenyl)-4-ethyl-1,3-dioxolan-2-yl-ethyl]-1-H-1,2,4-triazole
1-[2-(2,4-dichlorophenyl)-4-n-propyl-1,3-dioxolan-2-yl-ethyl]-1-H-1,2,4-triazole
N-(n-propyl)-N-(2,4,6-trichlorophenoxyethyl)-N'-imidazolylurea
1-(4-chlorophenoxy)-3,3-dimethyl-1-(1H-1,2,4-triazol-1-yl)-2-butanone
1-(4-chlorophenoxy)-3,3-dimethyl-1-(1H-1,2,4-triazol-1-yl)-2-butanol
alpha-(2-chlorophenyl)-alpha-(4-chlorophenyl)-5-pyrimidinemethanol
5-butyl-2-dimethylamino-4-hydroxy-6-methylpyrimidine
bis-(p-chlorophenyl)-3-pyridinemethanol
1,2-bis-(3-ethoxycarbonyl-2-thioureido)-benzene
1,2-bis-(3-methoxycarbonyl-2-thioureido)-benzene
and various fungicides, such as
dodecylguanidine acetate
3-[2-(3,5-dimethyl-2-oxycyclohexyl)-2-hydroxyethyl]-glutarimide
hexachlorobenzene
D,L-methyl-N-(2,6-dimethylphenyl)-N-(2-furoyl)-alanate
methyl D,L-N-(2,6-dimethylphenyl)-N-(2-methoxyacetyl)-alanate
N-(2,6-dimethylphenyl)-N-chloroacetyl-D,L-2-aminobutyrolactone
methyl DL-N-(2,6-dimethylphenyl)-N-(phenylacetyl)-alanate
5-methyl-5-vinyl-3-(3,5-dichlorophenyl)-2,4-dioxo-1,3-oxazolidine
3-(3,5-dichlorophenyl)-5-methyl-5-methoxymethyl-1,3-oxazolidine-2,4-dione
3-(3,5-dichlorophenyl)-1-isopropyl-carbamoylhydantoin
N-(3,5-dichlorophenyl)-1,2-dimethyl-cyclopropane-1,2-di-carboximide carboximide
2-cyano-N-(ethylaminocarbonyl)-2-(methoximino)-acetamide
1-(2-(2,4-dichlorophenyl)-pentyl)-1H-1,2,4-triazole
2,3-difluoro-alpha-(1H-1,2,4-triazol-1-yl-methyl)-benzhydryl alcohol.

The novel active ingredients are applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the novel active ingredients as possible.

For the preparation of solutions, emulsions, pastes and oil dispersions to be used direct or after emulsification in water, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, and N-methylpyrrolidone, and water are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

Examples of such formulations are given below.

I. 90 parts by weight of compound 1 is mixed with 100 parts by weight of N-methyl-alpha-pyrrolidone. A mixture is obtained which is suitable for application in the form of very fine drops.

II. 20 parts by weight of compound 52 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound 65 is dissolved in a mixture consisting of 30 parts by weight of cyclohexanone, 30 parts by weight of isobutanol, and 20 parts by weight of the adduct of 40 moles of ethylene oxide and 1 mole of castor oil. By pouring the solution into water and finely distributing it therein, an aqueous dispersion is obtained.

IV. 20 parts by weight of compound 64 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 20 parts by weight of compound 62 is well mixed with 3 parts by weight of the sodium salt of diisobutylnaphthalene-alpha-sulfonic naphthalene-alpha-sulfonic acid, 17 parts by weight of the sodium salt of a ligninsulfonic acid obtained from a sulfite waste liquor, and 60 parts by weight of powdered silica gel, and triturated in a hammer mill. By uniformly distributing the mixture in water, a spray liquor is obtained.

VI. 5 parts by weight of compound 1 is intimately mixed with 95 parts by weight of particulate kaolin. A dust is obtained containing 5% by weight of the active ingredient.

VII. 30 parts by weight of compound 52 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound 65 is intimately mixed with 30 parts of the sodium salt of a phenolsulfonic acid-urea-formaldehyde condensate, 2 parts of silica gel and 48 parts of water to give a stable aqueous dispersion.

IX. 20 parts of compound 62 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The following experiments demonstrate the biological action of the novel compounds. The agent used for comparison purposes was the prior art active ingredient N-trichloromethylthiotetrahydrophthalimide (A) particularly suitable for combatting Botrytis.

EXPERIMENT 1

Action on *Botrytis cinerea* in pimientos

Pimiento seedlings of the "Neusiedler Ideal Elite" variety were sprayed, after 4 to 5 leaves were well developed, to runoff with aqueous suspensions containing (dry basis) 80% of active ingredient and 20% of emulsifier. After the sprayed-on layer had dried, the plants were sprinkled with a conidial suspension of the fungus *Botrytis cinerea*, and placed at 22° to 24° C. in a chamber of high humidity. After 5 days, the disease had spread to such a great extent on the untreated plants that the necroses covered the major portion of the leaves.

The results of this experiment show that for instance compounds nos. 1, 52 and 66, applied as 0.05% spray liquors, had a better fungicidal action (e.g., 97%) than prior art active ingredient A (70%).

EXPERIMENT 2

Action on *Pyricularia oryzae* (protective)

Leaves of pot-grown rice seedlings of the "Bahia" variety were sprayed to runoff with aqueous emulsions consisting (dry basis) of 80% of active ingredient and 20% of emulsifier, and inoculated 24 hours later with an aqueous spore suspension of *Pyricularia oryzae*. The plants were then set up in climatic cabinets at 22° to 24° C. and a relative humidity of 95 to 99%. The extent of fungus spread was determined after 6 days.

The results of this experiment show that for example compounds nos. 63 and 65, applied as 0.05% spray liquors, had a good fungicidal action (e.g., 90%).

We claim:

1. An N-(azolylcarbamyl)-hydroxyamine of the formula

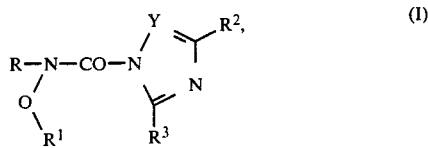

where R is a member selected from the group consisting of alkyl, alkenyl, alkoxyalkyl, cycloalkyl, alkyl substituted by cycloalkyl or cycloalkyl substituted by alkyl, each member consisting of not more than 12 carbon atoms, or phenyl, phenyl-$C_1$-$C_4$-alkyl, phenyl-$C_2$-$C_3$-alkenyl or phenoxy-$C_1$-$C_6$-alkyl, each of which is unsubstituted or substituted by halogen, cyano, nitro, trifluoromethyl, $C_1$-$C_4$-alkyl or $C_1$-$C_4$-alkoxy, $R^1$ is a member selected from the group consisting of alkyl, alkenyl, alkoxyalkyl, alkylthioalkyl, cycloalkyl or cycloalkylalkyl, each member consisting of not more than 12 carbon atoms, or benzyl which is unsubstituted or substituted by halogen, $C_1$-$C_4$-alkyl, $C_1$-$C_4$-alkoxy, trifluoromethyl, nitro or cyano, Y is CH or N, and $R^2$ and $R^3$ are identical or different and are each hydrogen or alkyl of 1 to 5 carbon atoms.

2. An N-(azolylcarbamyl)-hydroxylamine of the formula I as set forth in claim 1, where R and $R^1$ are ethyl; n-propyl; isopropyl; n-butyl; isobutyl; sec.-butyl; tert.-butyl; n-pentyl; 3-methylbut-1-yl; n-hexyl; 3,3-dimethylbut--methylbut--1-yl; n-heptyl; n-octyl; 2,4,4-trimethylpentyl; 2-ethylhexyl; n-decyl or n-dodecyl; cyclopropylmethyl; cyclopentyl; cyclohexyl; 4-methylcyclohexyl; cyclohexylmethyl; 4-tert.-butylcyclohexyl; 2-methoxyethyl; 2-ethoxyethyl; 2-propoxyethyl; 2-butoxyethyl; 3-methoxypropyl; 3-ethoxypropyl; 3-propoxypropyl; 3-butoxypropyl; allyl; but-2-en-1-yl; pent-2-en-yl; oct-2- en-1-yl; benzyl; 4-methylbenzyl; alpha-methylbenzyl; alpha-ethylbenzyl; 2-3- and 4-fluorobenzyl, 2-3- and 4-chlorobenzyl, 4-bromobenzyl; 3- and 4-trifluoromethylbenzyl; 4-tert.butylbenzyl; p-methoxybenzyl or 2,4-dichlorobenzyl; and R may also be phenyl; phenylethyl; 2-3- and 4-chlorophenyl; 4-methylphenyl; 4-methoxyphenyl; 4-trifluoromethyl; 2,4-dichloro- or 3,4-dichlorophenyl; phenoxyethyl; phenoxypropyl; phenoxybutyl; phenoxyhexyl; 4-fluorophenoxyethyl; 4-fluorophenoxybutyl; 2-3- or 4-chlorophenoxyethyl; -propyl, -butyl or -hexyl; 2,4-, 3,4- or 2,6-dichlorophenoxyethyl, -propyl, -butyl or -hexyl; 2,4,6-, 3,5,6- or 2,5,6-trichlorophenoxyethyl, -propyl or -butyl; 4-methoxyphenoxyethyl, -propyl or -butyl; 2-methyl-4,6-dichlorophenoxyethyl, -propyl or -butyl; 2,6-dichloro-4-bromophenoxyethyl, -propyl or -butyl; or 4-phenylphenoxyethyl, -propyl or -butyl; and $R^3$ are hydrogen, methyl or isopropyl.

3. A process for combatting fungi in plants, wherein the fungi or the plants or seed threatened by fungus attack are treated with a fungicidally effective amount of an N-(azolylcarbamyl)-hydroxylamine carbamyl)-hydroxylamine of the formula

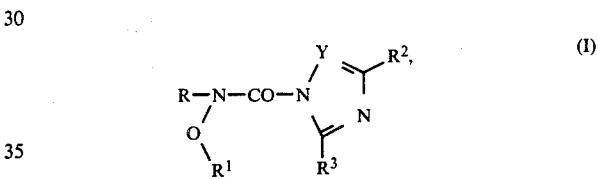

where R is a member selected from the group consisting of alkyl, alkenyl, alkoxyalkyl, cycloalkyl, alkyl cycloalkyl, alkyl substituted by cycloalkyl or cycloalkyl substituted by alkyl, each member consisting of not more than 12 carbon atoms, or phenyl, phenyl- $C_1$-$C_4$-alkyl, phenyl-$C_2$-$C_3$-alkenyl or phenoxy-$C_1$-$C_6$-alkyl, each of which is unsubstituted or substituted by halogen, cyano, nitro, trifluoromethyl, $C_1$-$C_4$-alkyl or $C_1$-$C_4$-alkoxy, $R^1$ is a member selected from the group consisting of alkyl, alkenyl, alkoxyalkyl, alkylthioalkyl, cycloalkyl or cycloalkylalkyl, each member consisting of not more than 12 carbon atoms, or benzyl which is unsubstituted or substituted by halogen, $C_1$-$C_4$-alkyl, $C_1$-$C_4$-alkoxy, trifluoromethyl, nitro or cyano, Y is CH or N, and $R^2$ and $R^3$ are identical or different and are each hydrogen or alkyl of 1 to 5 carbon atoms.

* * * * *

UNITED STATES PATENT AND TRADEMARK OFFICE
CERTIFICATE OF CORRECTION

PATENT NO. : 4,678,798

DATED : July 7, 1987

INVENTOR(S) : Costin RENTZEA et al.

It is certified that error appears in the above-identified patent and that said Letters Patent is hereby corrected as shown below:

Column 11, line 53 should read:

3,3-dimethylbut-1-yl; n-heptyl;

Signed and Sealed this

Twenty-ninth Day of March, 1988

Attest:

DONALD J. QUIGG

*Attesting Officer*　　　　　*Commissioner of Patents and Trademarks*